US012745991B2

(12) United States Patent
Forsvall

(10) Patent No.: US 12,745,991 B2
(45) Date of Patent: Sep. 29, 2026

(54) BIOPSY ARRANGEMENT

(71) Applicant: Xaga Surgical AB, Helsingborg (SE)

(72) Inventor: Andreas Forsvall, Helsingborg (SE)

(73) Assignee: Xaga Surgical AB, Helsingborg (SE)

( * ) Notice: Subject to any disclaimer, the term of this patent is extended or adjusted under 35 U.S.C. 154(b) by 679 days.

(21) Appl. No.: 18/027,444

(22) PCT Filed: Sep. 17, 2021

(86) PCT No.: PCT/EP2021/075680
§ 371 (c)(1),
(2) Date: Mar. 21, 2023

(87) PCT Pub. No.: WO2022/063704
PCT Pub. Date: Mar. 31, 2022

(65) Prior Publication Data

US 2024/0023943 A1 Jan. 25, 2024

(30) Foreign Application Priority Data

Sep. 23, 2020 (EP) .................................... 20197672

(51) Int. Cl.
*A61B 10/02* (2006.01)

(52) U.S. Cl.
CPC ................................ *A61B 10/0275* (2013.01)

(58) Field of Classification Search
CPC .................................................. A61B 10/0275
See application file for complete search history.

(56) References Cited

U.S. PATENT DOCUMENTS

2002/0173809 A1* 11/2002 Fleischman ............. A61F 2/064 606/153
2003/0229292 A1* 12/2003 Hibner ............... A61B 10/0275 600/566
2003/0229293 A1* 12/2003 Hibner ............... A61B 10/0283 600/567
2004/0073247 A1* 4/2004 Loshakove ............ A61B 17/11 606/184
2004/0073248 A1* 4/2004 Vargas .................... A61F 2/064 606/185
2005/0075655 A1* 4/2005 Bumbalough ..... A61B 17/1285 606/153

(Continued)

FOREIGN PATENT DOCUMENTS

JP 2005288187 A 10/2005
JP 2019531165 A 10/2019

OTHER PUBLICATIONS

International Search Report and Writen Opinon for PCT/EP2021/075680; Dec. 22, 2021; entire document.

*Primary Examiner* — Jeffrey G. Hoekstra
(74) *Attorney, Agent, or Firm* — Shore IP Group, PLLC; Howard J. Klein

(57) ABSTRACT

A biopsy needle arrangement comprises a needle sheath and a needle configured to lock a tip portion of the needle in relation to the sheath when the needle arrangement has obtained a closed state. The locking, which is obtained by configurations of sheath opening edges and proximal tip edges, between the tip portion of the needle and the sheath is in a third direction as well as in a rotational sense in that the tip cannot rotate around a longitudinal axis defined by a first direction.

14 Claims, 3 Drawing Sheets

(56) References Cited

U.S. PATENT DOCUMENTS

2005/0101983 A1* 5/2005 Loshakove ........ A61B 17/3496 606/185
2005/0154411 A1* 7/2005 Breznock ....... A61B 17/320016 606/184
2005/0177117 A1* 8/2005 Crocker ................ A61M 5/329 600/564
2006/0036272 A1* 2/2006 Solsberg ........ A61B 17/320016 606/170
2006/0074346 A1* 4/2006 Hibner ............... A61B 10/0275 600/568
2006/0200040 A1* 9/2006 Weikel ............... A61B 10/0275 606/167
2007/0185411 A1* 8/2007 Hibner ............... A61B 10/0275 600/568
2009/0204021 A1* 8/2009 Shabaz .............. A61B 10/0275 600/568
2009/0216152 A1* 8/2009 Speeg ................ A61B 10/0266 600/568
2009/0302089 A1* 12/2009 Harari .................. A61B 17/115 227/179.1
2011/0190802 A1* 8/2011 Mark ................. A61B 17/1611 606/171
2011/0201965 A1* 8/2011 Hibner ............... A61B 10/0275 600/567
2011/0208087 A1* 8/2011 Trezza, II ...... A61B 17/320016 600/567
2012/0330186 A1* 12/2012 Rhad .................. A61B 17/3403 600/567
2013/0006143 A1 1/2013 Neoh
2013/0150751 A1* 6/2013 Fiebig .................. A61B 8/0841 600/566
2016/0270810 A1* 9/2016 Vardi ............... A61B 17/32053
2018/0228476 A1 8/2018 Cannon
2019/0099199 A1* 4/2019 Levinson ........... A61B 17/3417
2019/0175842 A1 6/2019 Forsvall
2019/0247029 A1* 8/2019 Field ................ A61B 17/32053
2019/0321012 A1 10/2019 Ko
2020/0069330 A1* 3/2020 Butki ................. A61B 17/3403
2020/0146658 A1* 5/2020 Richardson, Jr. .. A61B 10/0275
2022/0280188 A1* 9/2022 Bhagavatula .... A61B 17/32053

* cited by examiner

BIOPSY ARRANGEMENT

CROSS-REFERENCE TO RELATED APPLICATIONS

This application is the § 371 National Stage Entry of International Application No. PCT/EP20201/075680 filed on Sep. 17, 2021, which claims the benefit of European Patent Application No. 20197672.7, filed on Sep. 23, 2020, the contents of which applications are herein incorporated by reference in their entirety.

FIELD OF THE INVENTION

The present invention relates to a needle arrangement for performing soft tissue biopsy.

BACKGROUND OF THE INVENTION

Within the field of medicine, needle arrangements for various purposes exist, for example needle arrangements for taking biopsy samples. A biopsy sampling arrangement includes, typically, in addition to a needle arrangement also some kind of actuator device that facilitates for an operator to push the biopsy needle into tissue and cut a biopsy sample of tissue. An important issue when performing biopsy sampling is, of course, to safeguard against accidental damage to a patient and to minimize the risks of infection.

Prior art biopsy needle arrangements (typically referred to as "tru cut" needle arrangements) have a drawback in that they collect a large amount of tissue on its way to a target area, where the actual biopsy tissue sample is to be obtained, inside a patient. During insertion, the biopsy needle arrangement will often encounter areas in which bacteria are present and such bacteria is often transported to areas where they will risk causing an infection.

Such a problem has typically been addressed by the use of antibiotics. However, with the increase of resistance to antibiotics, such a chemical way of addressing the problem has become less efficient and there is a demand for different technical solutions.

SUMMARY OF THE INVENTION

In view of the above, an object of the present disclosure is to overcome drawbacks related to prior art biopsy needle arrangements.

Such an object is achieved in one aspect by a biopsy needle arrangement comprising:

a needle sheath having proximal end and a distal end, the needle sheath constituting an elongated, along a first direction X, hollow tube having a sheath opening at the distal end of the needle sheath, the sheath opening being delimited by a first sheath opening edge that defines a first plane and a second sheath opening edge that defines a second plane, the first plane and the second plane intersecting with each other at an angle A along a first intersection line, a needle having proximal end and a distal end, the needle comprising an elongated, along the first direction X, shaft portion configured to fit inside and slide relative to the needle sheath, a tip portion connected to the shaft portion and located at the distal end of the needle, and a cavity formed by the shaft portion and extending in the first direction X, a second direction Y perpendicular to the first direction X and a third direction Z perpendicular to the first and second directions X, Y, the tip portion having a distal tip and a first proximal tip edge that defines a third plane and a second proximal tip edge that defines a fourth plane, the third plane and the fourth plane intersecting with each other at the angle A along a second intersection line, wherein:

the needle arrangement is configured to be in a closed state where the first sheath opening edge abuts the first proximal tip edge and the second sheath opening edge abuts the second proximal tip edge and the first intersection line coincides with the second intersection line.

Such a biopsy needle arrangement differs advantageously from prior art biopsy needle arrangements at least in that it is configured to lock the tip portion of the needle in relation to the sheath when the needle arrangement has obtained the closed state. The locking between the tip portion of the needle in relation to the sheath is obtained in the third direction Z as well as in a rotational sense in that the tip cannot rotate around a longitudinal axis defined by the first direction X. The locking ensures that there is no gap between the proximal end of the tip portion and the sheath opening when the edges of the sheath opening have been moved in the distal direction (here the first direction X) and cut a tissue sample lodged within the cavity. By avoiding a gap between the proximal end of the tip portion and the sheath opening, the needle arrangement of the present disclosure minimizes collection of bacteria during a biopsy procedure as discussed above. The locking function also enables multiple biopsies with maintained optimal closing of the needle arrangement.

The sheath opening edges may be configured such that the first intersection line avoids passing through the cavity, during relative sliding between the needle shaft portion and the sheath, for all positions of the first intersection line along the first direction X. Furthermore, the cavity in the needle may be delimited by at least a cavity bottom having a lowest bottom level in the third direction, and the first intersection line passing below, in the third direction, the lowest bottom level of the cavity bottom during relative sliding between the needle shaft portion and the sheath. Moreover, the second sheath opening surface may have an extension in the second direction, Y, that is equal to or less than the extension in the second direction Y of the cavity bottom.

That is, such configurations are stable in that they minimize any unwanted movement in the third direction Z during movement along the first direction X of the needle and the sheath when the biopsy procedure takes place. This avoids the risk of the biopsy tissue being lifted out of the cavity by the second sheath opening edge during the forward motion. With the second sheath opening edge being below the bottom level of the cavity, the biopsy tissue is pressed into the cavity by the first sheath opening edge and stays there. If the second sheath opening edge were to be configured at a level that is higher in relation to the bottom level of the cavity, it would provide an upwards directed force that would increase the risk of lifting the biopsy tissue upwards. This would result in a poor biopsy quality since a combination of upwards and downwards directed forces would become a pushing force forward which would lead to a poor cavity filling. By configuring the second sheath opening edge with a size that, in a view along the third direction, i.e. from above, has the same lateral limitation, i.e. width in a plane defined by the first X and second Y directions, as the needle, it has been found that the lifting forces acting upon the biopsy tissue in the cavity are eliminated and thus have no negative impact on the biopsy quality.

The cavity in the needle may be delimited by at least a distal cavity wall and a proximal cavity wall, the distal cavity wall being configured with a distal cavity wall angle in relation to the first direction, and the first sheath opening edge may be configured with a first sheath opening edge angle in relation to the first direction X that is equal to or smaller than the distal cavity wall angle.

Such configurations provide an efficient cut of tissue embedded within the cavity during the biopsy procedure when the sheath moves distally in the first direction X. Such an angular relationship ensures that a clean cut is made when the sheath first opening edge passes the distal cavity wall in the motion along the first direction X during the biopsy procedure.

The second sheath opening edge may be configured with a second sheath opening edge angle in relation to a direction that is opposite the first direction X that is greater than zero. For example, by configuring the second sheath opening edge with an angle in the interval 90° to 150° it has been found that the lifting forces acting upon the biopsy tissue in the cavity are eliminated and thus have no negative impact on the biopsy quality.

The hollow tube of the sheath and the sheath opening may have a circular cross-section in a plane defined by the second direction Y and the third direction Z, the shaft portion of the needle may comprise a circular cross-section in the plane defined by the second direction Y and the third direction Z, and the tip portion of the needle may comprise a circular cross-section in the plane defined by the second direction Y and the third direction Z.

That is, an overall or general circular cross-section of the biopsy needle arrangement, in a plane defined by the Y- and Z-directions, is advantageous in that it is simple to manufacture.

The tip portion may comprise a first face, a second face, and a third face, each face being configured such that it converges towards the distal tip and configured such that, during use in a biopsy procedure, and in a lefthanded orientation of the first direction X, the second direction Y, and the third direction Z, the first face is configured to push the tip portion counter to, or against, the third direction Z, the second face is configured to push the tip portion in, or along, the second direction and in the third direction Z, and the third face is configured to push the tip portion counter to, or against, the second direction Y and, in or along, the third direction Z.

In other words, in such embodiments, the tip portion can be seen as having a "plough" configuration. Such a configuration is advantageous in view of prior art biopsy needle arrangements.

Many of the prior art needle arrangements "dive" during the biopsy procedure, i.e. the needle tip is pushed downwards into the tissue during the forward motion of the needle. This may be beneficial from the amount of biopsy tissue obtained point of view as the cavity bottom is pressed upwards when the sheath is moved forward at the same time as the distal end of the sheath presses the tissue downwards. However, it has been recognized that this has an important drawback as the biopsy needle sometimes misses the target for the biopsy, and the tissue obtained thus originates from a location below the target.

With a more balanced force distribution acting upon the tip, due to the "plough" forming first, second and third faces of the tip portion, the movement of the needle forward in the first direction will have a straight character and thus hit the target for the biopsy better. Even though such a configuration may result in a slightly smaller amount of tissue obtained, the three-face configuration makes the needle move only a small distance downwards against the third direction Z due to the fact that the first face faces upwards in the third direction, and thus forces the tissue upwards in the third direction when the needle is moving forward, and thereby resulting in an optimization in terms of the filling the cavity with tissue.

In other embodiments, the tip portion may comprise a distal conical part ending in the distal tip, the distal conical part being configured such that the distal tip is offset in the third direction Z in relation to a central axis L along the first direction X such that, during use in a biopsy procedure, and in a lefthanded orientation of the first direction X, the distal conical part pushes the tip portion counter to, or against, the third direction Z.

A conical configuration of the tip portion provides the same advantageous movement as summarized above ion relation to embodiments with a "plough configuration". Moreover, a conical tip configuration has an advantageous effect in that it allows the needle tip portion to pass less traumatically through nerve tissue during the forward motion, as it lacks cutting edges, which when positioning the needle before actuation of the forward motion, allows nerves to be pushed away, i.e. laterally, minimizing the risk of cutting off the nerve tissue. For example, a biopsy needle arrangement having a conical tip may advantageously be used in a biopsy procedure towards the spinal cord, which to say the least involves extremely vital nerve tissue. A conical tip configuration achieves this advantage while at the same time achieving the advantage discussed above in connection with the "plough" configuration of improved filling of the cavity and slight downward movement. For example, by configuring the distal tip to be offset below the central axis L along the first direction X, against the third direction Z, by an appropriate distance, then during the needle movement in the first direction X, i.e. a stroke, the deviation of the distal tip in the third direction may be controlled to a desired, small, deviation. Furthermore, the tip may be configured sharp enough such that it may move non-traumatically through for example nerve tissue during a first step of insertion into a body and then cut tissue when moving fast through the tissue that is to be subject of the biopsy sampling.

DETAILED DESCRIPTION OF PREFERRED EMBODIMENTS

Figure 1A:
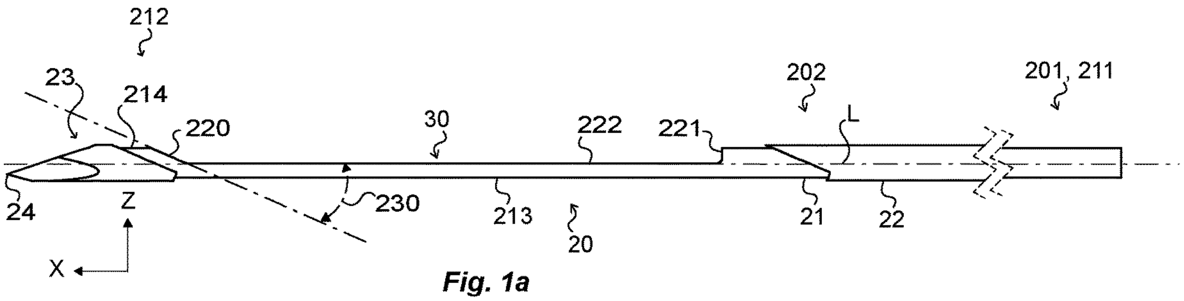
FIG. 1*a* is a schematically illustrated side view of a biopsy needle arrangement in an open state.

A biopsy needle arrangement 20 will now be exemplified with reference to FIGS. 1*a-d*, FIGS. 2*a-c* and FIGS. 3*a-c*. Reference will be made to individual features that each and every one have one and the same reference numeral throughout the referenced figures.

The biopsy needle arrangement 20 comprises a needle sheath 22 having proximal end 201 and a distal end 202. The needle sheath 22 constitutes an elongated, along a first direction X, hollow tube having a sheath opening 203 at the distal end 202 of the needle sheath 22. The sheath opening 203 is delimited by a first sheath opening edge 51 that defines a first plane 151 and a second sheath opening edge 52 that defines a second plane 152. The first plane 151 and the second plane 152 intersect with each other at an angle A along a first intersection line 153.

The biopsy needle arrangement 20 further comprises a needle 21 having proximal end 211 and a distal end 212. The needle 21 comprises an elongated, along the first direction X, shaft portion 213 configured to fit inside and slide relative to the needle sheath 22. A tip portion 23 is connected to the shaft portion 213 and located at the distal end 212 of the needle 21. A cavity 30 is formed by the shaft portion 213 and extends in the first direction X, a second direction Y perpendicular to the first direction X and a third direction Z perpendicular to the first and second directions X, Y.

The tip portion 23 has a distal tip 24 and a first proximal tip edge 61 that defines a third plane 161 and a second proximal tip edge 62 that defines a fourth plane 162. The third plane 161 and the fourth plane 162 intersect with each other at the angle A along a second intersection line 163.

The needle arrangement 20 is configured to be in a closed state where the first sheath opening edge 51 abuts the first proximal tip edge 61 and the second sheath opening edge 52 abuts the second proximal tip edge 62 and the first intersection line 153 coincides with the second intersection line 163.

A biopsy procedure using the biopsy needle arrangement 20 described herein involves a sequence of steps of moving the needle 21 and the needle sheath 22 in relation to each other and in relation to a body, e.g. a human or animal body, that is to be subject of the biopsy procedure. The actual movement of the needle 21 and the needle sheath 22 may be actuated by any suitable actuator arrangement. It is to be noted that any detailed description of such actuator arrangements is outside the scope of the present disclosure.

Figure 1B:
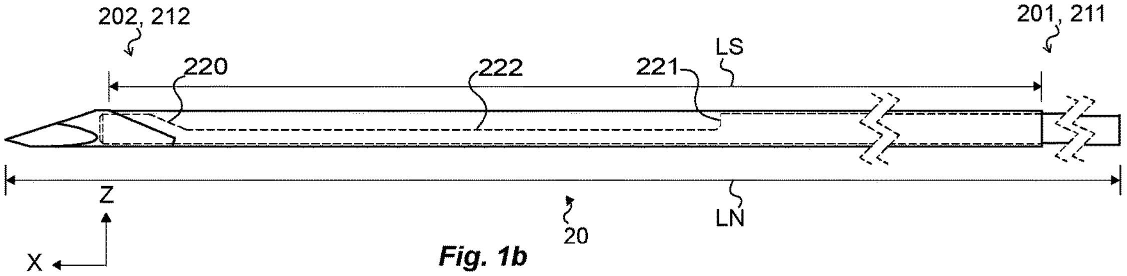
FIG. 1*b* is a schematically illustrated side view of a biopsy needle arrangement in a closed state.

Initially, the biopsy needle arrangement 20 is in a closed state as exemplified in FIG. 1*b*. In a first movement step, the biopsy needle arrangement 20 is inserted into the body that is to be subject of the biopsy procedure. In a second movement step, the needle 21 moves forward along the first direction X, piercing tissue that is to be subject of the biopsy. The forward movement of the needle 21 stops at a desired distance into the tissue, at which point the biopsy needle arrangement 20 is in the open state as exemplified in FIG. 1*a*. At this point, the cavity 30 becomes filled with tissue. In a third movement step, the needle sheath 22 moves forward along the first direction X until the biopsy needle arrangement 20 again obtains the closed state where the first sheath opening edge 51 abuts the first proximal tip edge 61 and the second sheath opening edge 52 abuts the second proximal tip edge 62 and the first intersection line 153 coincides with the second intersection line 163. During this third movement step, the needle sheath 22 makes a cutting action such that tissue becomes lodged inside the cavity 30. A fourth movement step then involves retracting the biopsy needle arrangement 20 backwards along the first direction X and thereby finalizing the biopsy procedure without the drawbacks associated with prior art biopsy arrangements.

As indicated in FIG. 1*b*, the needle 21 has a length, LN, that is greater than the length, LS, of the needle sheath 22. The first intersection line 153 may be transverse to, or perpendicular to, the first direction X. The first sheath opening edge 51 may face, or conform with, the first proximal tip edge 61. The second sheath opening edge 52 may face, or conform with, the second proximal tip edge 62 in the closed state.

The angle A may be less than 180°, and/or in the range 120°-180°, 100°-120°, 80°-100°, or 60°-80°. It has been found that the range 80°-100° is advantageous with respect to centring of the needle tip 24 and an angle of 90° is advantageous in terms of simplifying a manufacturing procedure creating the angle A, e.g., by milling or cutting. In other words, the angle A may be a right angle, or it may be an obtuse angle. A right angle provides a good balance between the centring ability at closing and the locking ability, while an obtuse angle provides a greater locking ability. Furthermore, it is specified that the first plane 151 and the second plane 152 intersect with each other at an angle A. In this context, the explicitly defined angles, or intervals of angles, are to be regarded as approximate.

The extension of the cavity 30 as defined above may be such that the cavity 30 has a length in the first direction X, a width in the second direction Y, and a height in the third direction Z.

As exemplified in the figures, the sheath opening 203 is delimited by a first sheath opening surface 53 that comprises the first sheath opening edge 51 and delimited by a second sheath opening surface 54 that comprises the second sheath opening edge 52. The surfaces 53, 54 may have an extension that relate to the thickness of the wall of the hollow tube of the sheath 22. However, the extension of the surfaces 53, 54 may be minimized during manufacturing by a sharpening step such that the edges 51, 52 become sharp edges.

As exemplified in the figures, the tip portion 23 comprises a first proximal tip surface 63 that comprises the first proximal tip edge 61, and a second proximal tip surface 64 that comprises the second proximal tip edge 62.

The sheath opening edges 51, 52 are configured such that the first intersection line 153 avoids passing through the cavity 30, during relative sliding between the needle shaft portion 213 and the sheath 22, for all positions of the first intersection line 153 along the first direction X.

In other words, the sheath opening edges 51, 52 being configured such that the first intersection line 153 avoids passing through the cavity 30 is understood to encompass the first intersection line 153 and the cavity 30 being separated, being spaced apart, or forming a separation, transversely to the first direction X in the closed state.

As illustrated, the cavity 30 in the needle 21 is delimited by at least a cavity bottom 222 having a lowest bottom level in the third direction Z. Then, the first intersection line 153 passes below, in the third direction Z, the lowest bottom level of the cavity bottom 222 during relative sliding between the needle shaft portion 213 and the sheath 22.

In other words, the first intersection line 153 passing below, in the third direction Z, the lowest bottom level of the cavity bottom 222 is understood to encompass the first intersection line 153 and the cavity 30, or the lowest bottom level of the cavity bottom 222, being separated, being spaced apart, or forming a separation, in the third direction Z in the closed state. Furthermore, as exemplified here, advantageous embodiments are those where the width or extension, in the second direction Y, of the second sheath opening surface 54 is equal to or less than the width or extension, in the second direction Y, of the cavity bottom 222. Such a configuration minimizes lifting forces, i.e. forces acting upward in the third direction Z, during movement of the needle arrangement in the biopsy procedure.

As exemplified, the intersection lines 153, 163 are parallel to the second direction Y. In such a case, the first plane 151, the second plane 152, the third plane 161 and the fourth plane 162 may have respective orientations or angles relative to the first direction X as follows: the first plane 151 and the third plane 161 may have an angle 154 in the interval 10° to 45° relative to the first direction X, and the second plane 152 and the fourth plane 162 may have an angle 155 in the interval 90° to 150° relative to a direction that is opposite the first direction X. Moreover, as discussed above, since an advantageous value for the intersecting angle A is 90°, this means that there are, given these intervals for the angles 154, 155, several corresponding advantageous values also for the angles 154, 155 of the planes 151, 152, 161, 162 relative to the first direction X. For example, the following table provides three sets of such advantageous angles:

| Angle 154 | Angle 155 |
|---|---|
| 20° | 110° |
| 23° | 113° |
| 30° | 120° |

Figure 1C:
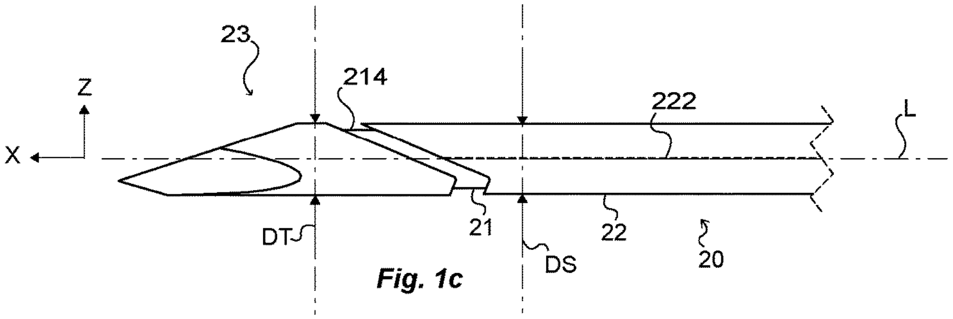
FIGS. 1*c* and 1*d* are schematically illustrated side views of a distal end of a biopsy needle arrangement.
Figure 1D:
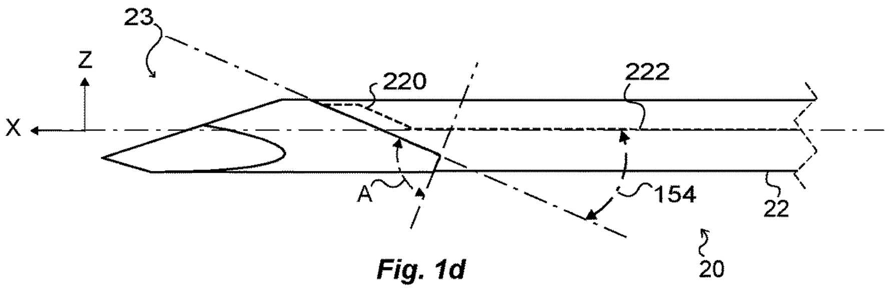

As indicated in FIG. 1*c*, the shaft portion 213 comprises an intermediate portion 214 between the cavity 30 and the tip portion 23, wherein the intermediate portion 214 is positioned inside and conforms to the needle sheath 22 in the closed state. Such an intermediate portion has an extension in the first direction in order to allow the sheath opening edges 51, 52, during the forward motion cutting the tissue sample in the cavity 30, to make a clean cut of the tissue in the cavity 30. Removal of tissue from the cavity 30 may be facilitated by the existence of such an intermediate portion 214. Nevertheless, alternative configurations of the needle arrangement 20 may be without such an intermediate portion 214 whereby the cavity 30 ends flush with the proximal tip edge 61.

The cavity 30 in the needle 21 is delimited by at least a distal cavity wall 220 and a proximal cavity wall 221. The distal cavity wall 220 is configured with a distal cavity wall angle 230 in relation to the first direction X and the first sheath opening edge 51 is configured with a first sheath opening edge angle 154 in relation to the first direction X that is equal to or smaller than the distal cavity wall angle 230. Such a configuration between the angle 230 of the distal cavity wall 220 and the first sheath opening edge angle 154 allows the sheath opening edges 51, 52, during the forward motion cutting the tissue sample in the cavity 30, to make a clean cut of the tissue in the cavity 30.

It has been found that an advantageous limit on the angle 230 of the distal cavity wall 220 is 45° (although angles in the interval 45° to 60° may also be advantageous) and it is more or less independent of the first sheath opening edge angle 154. Such an angle mitigates any effects of an accidental collision between the first sheath opening edge 51 and the distal cavity wall 220 during the forward movement of the sheath 22.

The second sheath opening edge 52 is configured with a second sheath opening edge angle 155 in relation to a direction that is opposite the first direction X that is greater than zero. Advantageous values for the second sheath opening edge angle 155 have been exemplified above.

As exemplified in the figures, the hollow tube of the sheath 22 and the sheath opening 203 have a circular cross-section in a plane defined by the second direction Y and the third direction Z, the shaft portion 213 of the needle 21 comprises a circular cross-section in the plane defined by the second direction Y and the third direction Z, and the tip portion 23 of the needle 21 comprises a circular cross-section in the plane defined by the second direction Y and the third direction Z. However, other Y/Z cross-sections are not excluded, for example an oval cross-section.

The tip portion 23 has an extension DT in the plane defined by the second direction Y and the third direction Z that is greater than or equal to a transverse extension DS in the plane defined by the second direction Y and the third direction Z of the sheath opening 203.

Additionally or alternatively, at each point where the first sheath opening edge 51 abuts the first proximal tip edge 61 in the closed state, the tip portion 23 may have a radial extension that is greater than or equal to the corresponding extension of the sheath opening 203. Similarly, at each point where the second sheath opening edge 52 abuts the second proximal tip edge 62 in the closed state, the tip portion 23 may have a radial extension that is greater than or equal to the corresponding extension of the sheath opening 203. Here, the radial extension is understood to be with respect to the first direction X, or in a plane defined by the second direction Y and the third direction Z.

In other words, the outside of the biopsy needle arrangement 20 should be as smooth as possible, which means that the relevant parts (sheath 22 and tip portion 23) should advantageously have the same diameter. However, from a manufacturing perspective, the tolerance in terms of the extensions of the parts should be such that the extension of the tip portion 23 is larger. A reason for this is that such a relation reduces the risk collecting foreign material such as bacteria during the first step of the biopsy procedure (as described above) and also reduces the risk of collecting bacteria during repeated passages in contrast to a configuration where the sheath 22 has a greater extension than the extension of the tip portion 23. Ideally, however, the same diameter and perfect fit between the parts is desirable. The parts should ideally fit in the closed state and when the parts are pressed together.

As illustrated in FIGS. 1*a-d* and FIGS. 2*a-c*, the tip portion 23 comprises a first face 251, a second face 252, and a third face 253. Each face 251, 252, 253 is configured such that it converges towards the distal tip 24 and configured such that, during use in the biopsy procedure, and in a lefthanded orientation of the first direction X, the second direction Y, and the third direction Z, the first face 251 is configured to push the tip portion 23 counter to, or against, the third direction Z, the second face 252 is configured to push the tip portion 23 in, or along, the second direction Y and in the third direction Z, and the third face 253 is configured to push the tip portion 23 counter to, or against, the second direction Y and, in or along, the third direction Z.

Such a configuration provides the biopsy needle arrangement 20 with a ploughing character that provides a more balanced force distribution acting upon the tip portion 23, due to the "plough" forming first, second and third faces 251, 252, 253 of the tip portion 23, the movement of the needle 21 forward in the first direction X will have a straight character and thus hit the target for the biopsy better. Even though such a configuration may result in a slightly smaller amount of tissue obtained, the three-face configuration makes the needle 21 move straight or only a small distance downwards against the third direction Z due to the fact that the first face 251 faces upwards in the third direction Z forming an acute angle 261 with respect to the first direction X, and thus forces the tissue upwards in the third direction Z when the needle tip portion 23 is moving forward in the first direction X, and thereby resulting in an optimization in terms of the filling the cavity 30 with tissue.

Variations of the example in FIGS. 1*a-d* and FIGS. 2*a-c* may be tip portions having a larger number of faces, for example a tip configuration having one face similar to the first face 251 and three or more faces forming the "plough" shape in a similar manner as the second and third faces 252, 253.

Figure 2A:
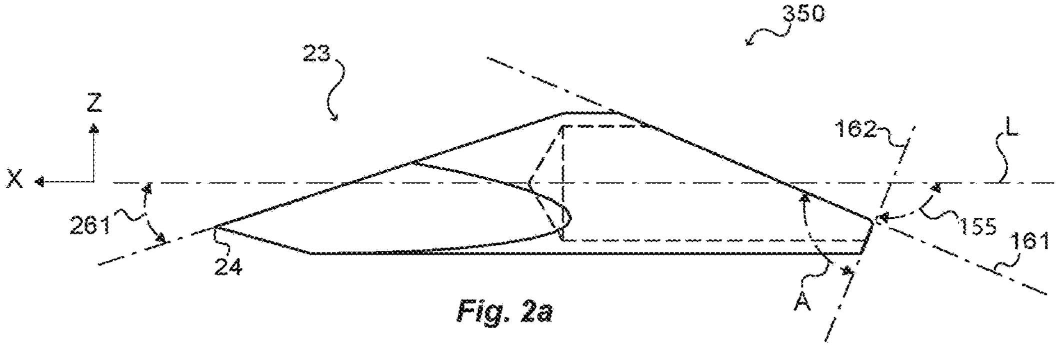
FIG. 2*a* is a schematically illustrated side view of a tip portion of a biopsy needle arrangement.
Figure 2B:
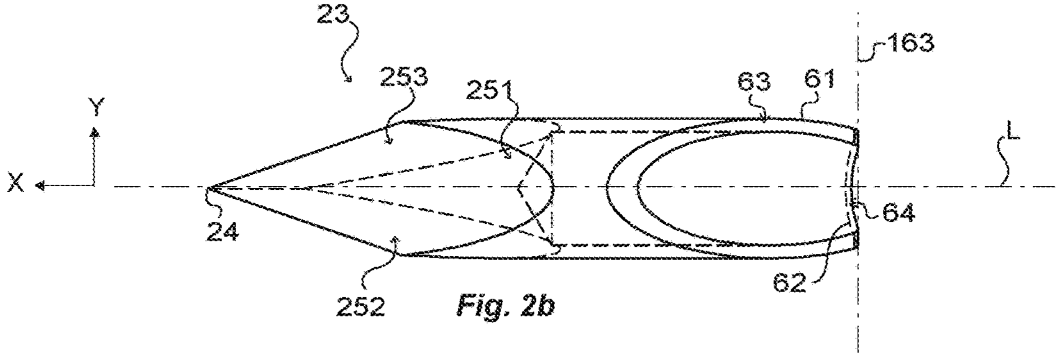
FIG. 2*b* is a schematically illustrated top view of a tip portion of a biopsy needle arrangement.
Figure 2C:
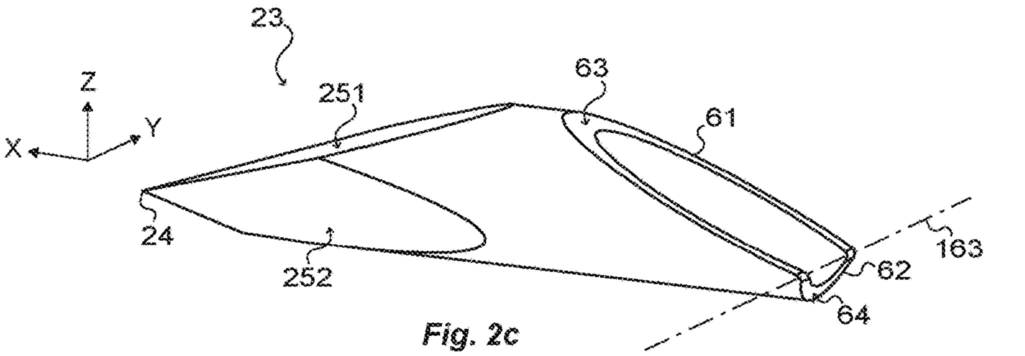
FIG. 2*c* is a schematically illustrated perspective view of a tip portion of a biopsy needle arrangement.
Figure 2D:
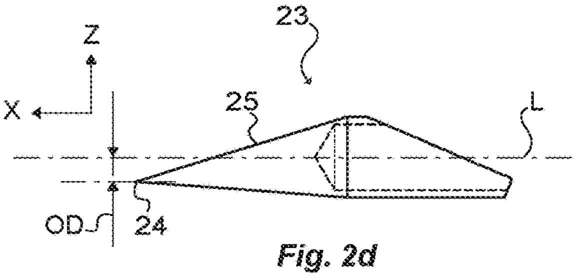
FIG. 2*d* is a schematically illustrated side view of a tip portion of a biopsy needle arrangement.
Figure 2E:
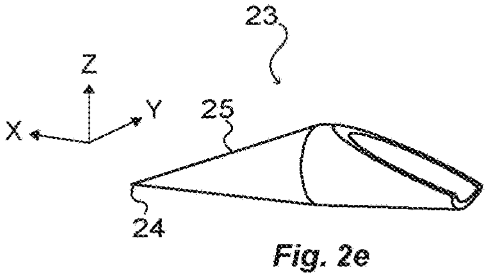
FIG. 2*e* is a schematically illustrated perspective view of a tip portion of a biopsy needle arrangement.
Figure 3A:
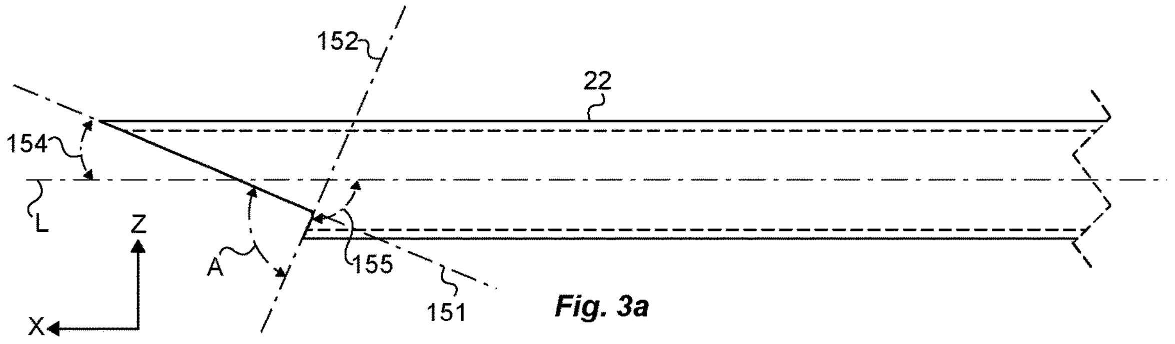
FIG. 3*a* is a schematically illustrated side view of a needle sheath of a biopsy needle arrangement.
Figure 3B:
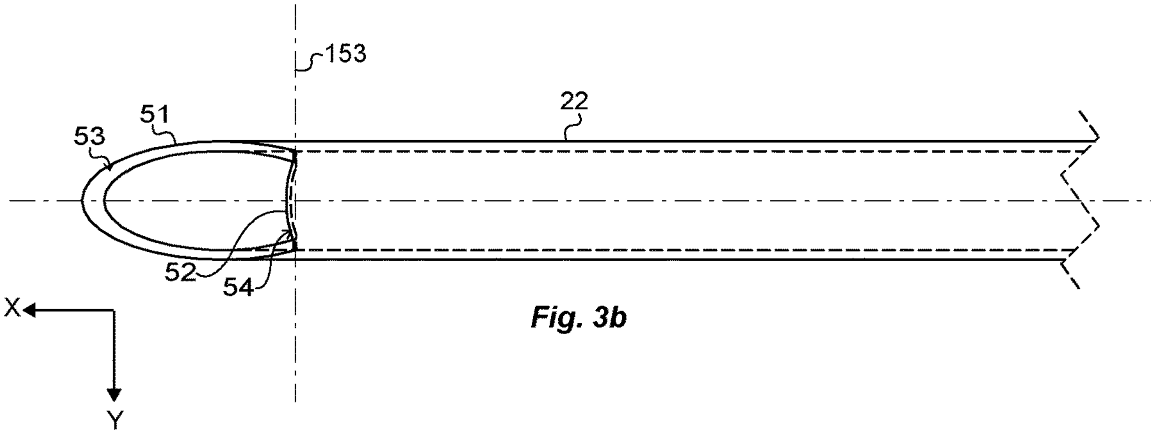
FIG. 3*b* is a schematically illustrated bottom view of a needle sheath of a biopsy needle arrangement.
Figure 3C:
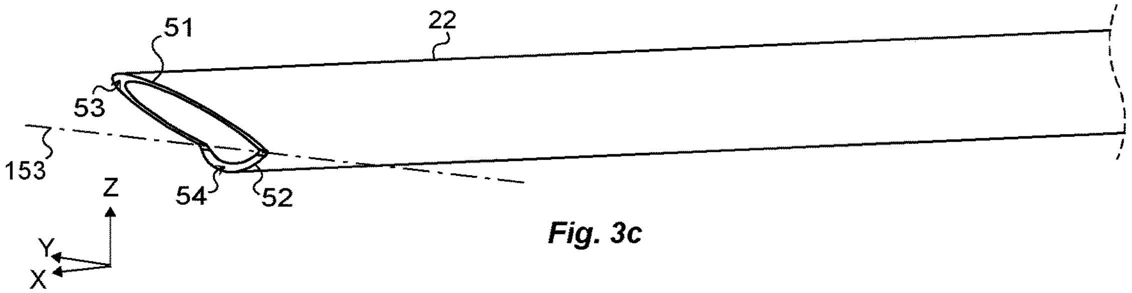
FIG. 3*c* is a schematically illustrated perspective view of a needle sheath of a biopsy needle arrangement.

A further alternative configuration of the tip portion 23 is exemplified in FIGS. 2*d* end 2*e*. In other words, the biopsy needle arrangement 20 may comprise a tip portion 23 that comprises a distal conical part 25 ending in the distal tip 24. Such a distal conical part 25 may be configured such that the distal tip 24 is offset in the third direction Z in relation to a central axis L along the first direction X such that, during use in the biopsy procedure, and in a lefthanded orientation of the first direction X, the distal conical part 25 pushes the tip portion 23 counter to, or against, the third direction Z.

Such a configuration provides the biopsy needle arrangement 20 with a ploughing character similar to that of the "plough" configuration described above. For example, by configuring the distal tip to be offset below the central axis L along the first direction X, against the third direction Z, by an appropriate distance OD, then during the needle movement in the first direction X, i.e. a stroke, of e.g. 2 cm, the deviation of the distal tip may be less than 1 mm, which is a typical acceptable or desired deviation.

The invention claimed is:

1. A biopsy needle arrangement comprising:

a needle sheath having proximal end and a distal end, the needle sheath constituting an elongated, along a first direction, hollow tube having a sheath opening at the distal end of the needle sheath;

the sheath opening being delimited by a first sheath opening edge that defines and is disposed in a first plane and a second sheath opening edge that defines and is disposed in a second plane that is inclined relative to the first plane, the first plane and the second plane intersecting with each other at an angle along a first intersection line; and a needle having proximal end and a distal end, the needle comprising an elongated, along the first direction, shaft portion configured to fit inside of, and to slide relative to, the needle sheath; a tip portion connected to the shaft portion and located at the distal end of the needle; and a cavity formed by the shaft portion and extending in the first direction, a second direction perpendicular to the first direction, and a third direction perpendicular to the first and second directions;

the tip portion having a distal tip and a first proximal tip edge that defines and is disposed in a third plane and a second proximal tip edge that defines and is disposed in a fourth plane that is inclined relative to the third plane, the third plane and the fourth plane intersecting with each other at the angle along a second intersection line;

wherein:

the needle arrangement is configured to be in a closed state where the first sheath opening edge abuts the first proximal tip edge and the second sheath opening edge abuts the second proximal tip edge and the first intersection line coincides with the second intersection line.

2. The biopsy needle arrangement of claim 1, wherein:

the sheath opening is delimited by a first sheath opening surface that comprises the first sheath opening edge, and the sheath opening is delimited by a second sheath opening surface that comprises the second sheath opening edge.

3. The biopsy needle arrangement of claim 1, wherein:

the tip portion comprises a first proximal tip surface that comprises the first proximal tip edge, and the tip portion comprises a second proximal tip surface that comprises the second proximal tip edge.

4. The biopsy needle arrangement of claim 1, wherein:

the first and second sheath opening edges are configured such that the first intersection line avoids passing through the cavity, during relative sliding between the needle shaft portion and the sheath, for all positions of the first intersection line along the first direction.

5. The biopsy needle arrangement of claim 4, wherein:

the cavity in the needle is delimited by at least a cavity bottom having a lowest bottom level in the third direction, and the first intersection line passes below, in the third direction, the lowest bottom level of the cavity bottom during relative sliding between the needle shaft portion and the sheath.

6. The biopsy needle arrangement of claim 1, wherein the first and second intersection lines are parallel to the second direction.

7. The biopsy needle arrangement of claim 1, wherein:

the sheath opening is delimited by a first sheath opening surface that comprises the first sheath opening edge, the cavity in the needle is delimited by at least a cavity bottom having a lowest bottom level in the third direction, and the second sheath opening surface has an extension in the second direction that is equal to or less than the extension in the second direction of the cavity bottom.

8. The biopsy needle arrangement of claim 1, wherein the shaft portion comprises an intermediate portion between the cavity and the tip portion, wherein the intermediate portion is positioned inside and conforms to the needle sheath in the closed state.

9. The biopsy needle arrangement of claim 1, wherein:

the cavity in the needle is delimited by at least a distal cavity wall and a proximal cavity wall, the distal cavity wall being configured with a distal cavity wall angle in relation to the first direction, and the first sheath opening edge is configured with a first sheath opening edge angle in relation to the first direction that is equal to or smaller than the distal cavity wall angle.

10. The biopsy needle arrangement of claim 1, wherein:

the second sheath opening edge is configured with a second sheath opening edge angle in relation to a direction that is opposite to the first direction that is in the interval 90° to 150°.

11. The biopsy needle arrangement of claim 1, wherein the hollow tube of the sheath and the sheath opening have a circular cross-section in a plane defined by the second direction and the third direction, the shaft portion of the needle comprises a circular cross-section in the plane defined by the second direction and the third direction, and the tip portion of the needle comprises a circular cross-section in the plane defined by the second direction and the third direction.

12. The biopsy needle arrangement of claim 1, wherein the tip portion has an extension in the plane defined by the second direction and the third direction that is greater than or equal to a transverse extension in the plane defined by the second direction and the third direction of the sheath opening.

13. The biopsy needle arrangement of claim 1, wherein the tip portion comprises a first face, a second face, and a third face, each face being configured such that it converges towards the distal tip and configured such that, during use in a biopsy procedure, and in a lefthanded orientation of the first direction, the second direction, and the third direction, the first face is configured to push the tip portion counter to, or against, the third direction, the second face is configured to push the tip portion in, or along, the second direction and in the third direction, and the third face is configured to push the tip portion counter to, or against, the second direction and, in or along, the third direction.

14. The biopsy needle arrangement of claim 1, wherein the tip portion comprises a distal conical part ending in the distal tip, the distal conical part being configured such that the distal tip is offset in the third direction in relation to a central axis along the first direction such that, during use in a biopsy procedure, and in a lefthanded orientation of the first direction, the distal conical part pushes the tip portion counter to, or against, the third direction.

* * * * *